United States Patent [19]

Meyer et al.

[11] Patent Number: 5,220,062

[45] Date of Patent: Jun. 15, 1993

[54] PROCESS FOR THE PREPARATION OF BENEZENESULFONAMIDES

[75] Inventors: Willy Meyer, Riehen; Urs Siegrist, Eiken, both of Switzerland

[73] Assignee: Ciba-Geigy Corporation, Ardsley, N.Y.

[21] Appl. No.: 875,855

[22] Filed: Apr. 29, 1992

[30] Foreign Application Priority Data

May 6, 1991 [CH] Switzerland ............... 1347/91

[51] Int. Cl.$^5$ ............... C07C 303/38; C07C 311/15; C07C 309/86; C07C 309/87
[52] U.S. Cl. ............... 564/90; 562/74; 562/830; 562/833
[58] Field of Search ............... 562/74, 830, 833; 564/90

[56] References Cited

U.S. PATENT DOCUMENTS 4,671,819  6/1987  Meyer et al. ............... 71/93

5,104,440  4/1992  Meyer et al. ............... 71/92

*Primary Examiner*—Allen J. Robinson
*Assistant Examiner*—P. O'Sullivan
*Attorney, Agent, or Firm*—Kevin T. Mansfield; Edward McC. Roberts

[57] ABSTRACT

There is disclosed a multi-step process for the preparation of benzenesulfonamides of general formula

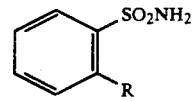

wherein R is 3,3-difluorobutyl or 3,3-difluorobuten-1-yl.

The benzenesulfonamides obtainable by the process of the invention are intermediates for the synthesis of herbicidally active sulfonyl ureas.

7 Claims, No Drawings

PROCESS FOR THE PREPARATION OF BENEZENESULFONAMIDES

The present invention relates to a process for the preparation of benzenesulfonamides of general formula

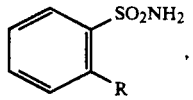

wherein R is 3,3-difluorobutyl (—CH₂—CH₂—CF₂—CH₃) or 3,3-difluorobuten-1-yl (—CH=CH—CF₂—CH₃).

The benzenesulfonamides of formula I are useful intermediates for the synthesis of herbicidally active N-phenylsulfonyl-N'-pyrimidinyl- and -N'-triazinylsulfonylureas. Sulfonylureas are disclosed in, inter alia, European patent applications EP-A-0 120 814 and EP-A-0 102 925. The benzenesulfonamides of formula I are particularly suitable for the synthesis of N-[2-(3,3-difluorobutyl)phenyl]-N'-(4-methoxy-6-methyl-1,3,5-triazin-2-yl)urea and N-[2-(3,3-difluorobuten-1-yl)phenyl]-N'-(4-methoxy-6-methyl-1,3,5-triazin-2-yl)urea.

The benzenesulfonamides of formula I are prepared in the practice of this invention by converting a 2-(3-oxobuten-1-yl)benzenesulfonic acid salt of formula II

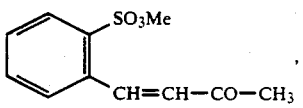

wherein Me is an alkali metal ion or an ammonium ion, by catalytic hydrogenation into a 2-(3-oxobutyl)benzenesulfonic acid salt of formula III

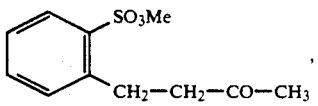

wherein Me has the above meaning, converting said acid salt by reaction with an inorganic acid chloride into a 2-(3-oxobutyl)benzenesulfonyl chloride of formula IV

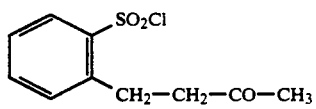

then converting said sulfonyl chloride with phosphorus pentachloride into a mixture of benzenesulfonyl chlorides of formula V

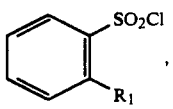

wherein R₁ is 3-chloro-2-buten-1-yl

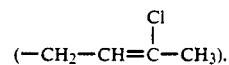

3-chloro-3-buten-1-yl

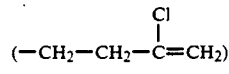

or 3,3-dichlorobutyl (—CH₂—CH₂—CCl₂—CH₃), reacting said mixture with hydrogen fluoride to give a mixture of 2-(3,3-difluorobutyl)-benzenesulfonyl halides of formula VI

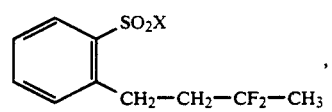

wherein X is chloro or fluoro, and converting said mixture either a) by reaction with ammonia into the 2-(3,3-difluorobutyl)benzenesulfonamide of formula Ia

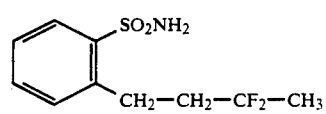

or b) initially with a brominating agent (1,3-dibromo-5,5-dimethylhydantoin) into a mixture of 2-(1-bromo-3,3-difluorobutyl)benzenesulfohalides of formula VII

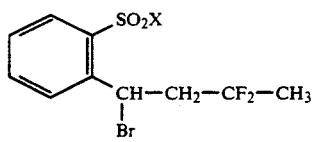

wherein X is fluoro or chloro, and then converting this mixture by further reaction with ammonia into the 2-(1-bromo-3,3-difluorobutyl)sulfonamide of formula VIII

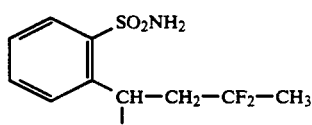

which is then dehydrobrominated to 2-(3,3-difluorobuten-1-yl)benzenesulfonamide of formula Ib

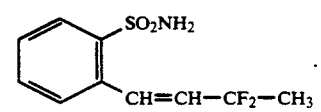

The starting sulfonic acid salts of formula II can be prepared by the method described in European patent application EP-A-0 102 925 by first diazotising orthanilic acid and then reacting the diazonium salt with methyl vinyl ketone in the presence of a palladium catalyst.

The catalytic hydrogenation of the benzenesulfonic acid salt of formula II is conveniently carried out in an inert solvent in the presence of a noble metal catalyst. Suitable solvents are water, acetic acid and lower alkanols, preferably methanol and ethanol. It is preferred to carry out the catalytic hydrogenation of the sulfonic acid salts of formula II in water. Preferred noble metal catalysts are palladium on carbon or platinum on carbon. The reaction temperature is normally in the temperature range from 0° to 50° C. and the pressure is in the range from 1 to 5 bar. It is preferred to carry out the reaction at room temperature and under normal pressure.

Suitable inorganic acid chlorides for converting the sulfonic acid salts of formula III into the corresponding acid chlorides are phosgene, thionyl chloride and phosphorus pentachloride. It is preferred to react the sulfonic acid salts of formula III with phosgene. These acid chlorides are used in stoichiometric proportion or in excess of stoichiometric proportion. The molar ratio of sulfonic acid salt of formula III to inorganic acid chloride is usually 1:1–1.5. The reaction is conveniently carried out in an inert organic solvent, preferably in an aliphatic or aromatic hydrocarbon or a halogenated hydrocarbon. Suitable solvents are hexane, cyclohexane, chloroform, carbon tetrachloride, toluene and chlorobenzene. The preferred solvent is chlorobenzene. The reaction can be carried out in the temperature range from 20°–130° C. The preferred temperature range for carrying out the reaction is from 70°–90° C. It is expedient to carry out the reaction in the presence of a catalytic amount of N,N-dimethylformamide.

The reaction of the sulfonyl chloride of formula IV with phosphorus pentachloride is conveniently carried out in an inert solvent. Suitable solvents are aliphatic and aromatic hydrocarbons and halogenated hydrocarbons, typically methylene chloride, chloroform, carbon tetrachloride, toluene and chlorobenzene. It is preferred to carry out the reaction in methylene chloride. The reaction temperature may vary in the range from 0°–100° C. and is preferably in the range from 20°–40° C. The phosphorus pentachloride is used in stoichiometric proportion or in an excess of up to 20%.

The reaction of the sulfonyl chloride of formula IV with phosphorus pentachloride yields a mixture consisting of 2-(3-chloro-2-buten-1-yl)benzenesulfonyl chloride, 2-(3-chloro-3-buten-1-yl)benzenesulfonyl chloride and 2-(3,3-dichlorobutyl)benzenesulfonyl chloride. The composition of the mixture will depend on the chosen reaction conditions. Normally more 2-(3,3-dichlorobutyl)benzenesulfonyl chloride is obtained under mild reaction conditions, whereas more severe reaction conditions will promote the formation of the 2-(3-chlorobutenyl)benzenesulfonyl chlorides. In this reaction, the cis- as well as the trans-isomers of 2-(3-chloro-2-buten-1-yl)benzenesulfonyl chloride are obtained. However, the subsequent reaction of the mixture of compounds of formula V with hydrogen fluoride gives the 2-(3,3-difluorobutyl)benzenesulfonyl halide of formula VI in excellent yield.

The reaction of benzenesulfonyl chlorides of formula V with hydrogen fluoride is conveniently carried out in an inert solvent. Either excess hydrogen fluoride acts as sole solvent, or an additional inert solvent such as n-hexane, cyclohexane, toluene or chlorobenzene can be used. The reaction temperature may vary over a wide range, and is suitably from −50° to +100° C. The reaction is preferably carried out in the temperature range from 0°−50° C. The reaction is conveniently carried out by mixing the reactants at low temperature and then heating the mixture in a closed system to the reaction temperature, whereupon increased pressure resulting from the formation of hydrogen chloride builds up in the reactor. As the hydrogen chloride may lead to secondary reactions, it is best removed from the reaction mixture from time to time.

The reaction of the benzenesulfonyl halide of formula VI with ammonia is conveniently carried out by introducing ammonia into a solution of the sulfonyl halide of formula VI in an inert solvent. Suitable solvents are aliphatic or aromatic hydrocarbons, halogenated hydrocarbons and ethers. Suitable solvents are typically n-hexane, cyclohexane, toluene, chlorobenzene, diethylether, tetrahydrofuran or dioxane. The reaction temperature may be in the range from room temperature to 50° C. The reaction can also be carried out in a two-phase reaction medium by reacting a solution of the sulfonyl halide of formula VI in toluene with an aqueous solution of ammonia.

The bromination of the sulfonyl halide of formula VI is preferably carried out in an inert solvent, suitably an aliphatic or aromatic hydrocarbon or a halogenated hydrocarbon. Preferred solvents are aliphatic halogenated hydrocarbons such as chloroform and carbon tetrachloride. Suitable brominating agents are bromine, and dehydrobrominating agents such as N-bromosuccinimide and 1,3-dibromo-5,5-dimethylhydantoin. The brominating agent is used in stoichiometric proportion or in an excess of up to 20%. It is useful to carry out the reaction in the presence of a radical former such as UV light or azoisobutyronitrile.

The further reaction of the benzenesulfonyl halide of formula VII with ammonia is conveniently carried out in an inert solvent, as in an ether or a hydrocarbon. Suitable solvents are diethyl ether, tetrahydrofuran, dioxane, pentane, hexane, cyclohexane and also acetonitrile. The reaction is conveniently carried out by introducing ammonia into a solution of the benzenesulfonyl halide of formula VII in one of the above mentioned solvents. The ammonia is used in stoichiometric proportion or in a small excess of up to 10%.

The intermediates of formulae III, IV, V, VI, VII and VIII formed in the process of this invention are novel compounds and also fall within the scope of the invention.

Using readily accessible starting materials, the process of this invention makes it possible to prepare the benzenesulfonamides of formula I in simple manner and in good yield. The benzenesulfonamides of formula I can be converted in per se known manner into herbicidally active sulfonyl ureas, suitably by reaction with 2-alkoxycarbonylaminopyrimidines or -triazines or 2-phenoxycarbonylaminopyrimidines or -triazines.

The following Examples illustrate the invention in more detail.

EXAMPLE 1

Preparation of sodium 2-(3-oxobutyl)benzenesulfonate 325 g of sodium 2-(3-oxobuten-1-yl)benzenesulfonate (73%) are dissolved in 2700 ml of water and, after addition of 20 g of a platinum/carbon catalyst (5%), the solution is hydrogenated with hydrogen. After 2 hours the uptake of hydrogen ceases. Altogether 20.5 l of hydrogen are taken up. The catalyst is then removed by filtration and the filtrate is evaporated to dryness. The residue is taken up in chlorobenzene and freed from water by azeotropic distillation. The resultant suspension of sodium 2-(3-oxobutyl)benzenesulfonate can be used direct for the subsequent phosgenation.

EXAMPLE 2

Preparation of 2-(3-oxobutyl)benzenesulfonyl chloride 10 ml of dimethyl formamide are added to the suspension of sodium 2-(3-oxobutyl)benzenesulfonate in chloroform obtained in Example 1 and then 197 g of phosgene are introduced at 75°-80° C. over 5 hours. Then nitrogen is blown through the reaction mixture for 2 hours, whereupon the temperature falls to 20°-25° C. The reaction mixture is then filtered, evaporated to dryness, and the residue is recrystallised from cyclohexane. Yield: 163 g of 2-(3-oxobutyl)benzenesulfonyl chloride of m.p. 67°-68° C.

EXAMPLE 3

Preparation of a mixture consisting of 2-(3,3-dichlorobutyl)benzenesulfonyl chloride, 2-(3-chloro-2-buten-1-yl)benzenesulfonyl chloride and 2-(3-chloro-3-buten-1-yl)benzenesulfonyl chloride 102.7 g of phosphorus pentachloride are added in portions to a solution of 116 g of 2-(3-oxobutyl)benzenesulfonyl chloride in 700 ml of dichloromethane at 20°-30° C. over 1 hour, and the reaction mixture is then stirred for 15 hours at 20°-25° C. The reaction mixture is thereafter evaporated to dryness and the residue is taken up in chloroform. The solution is evaporated to dryness, affording 118 g of a mixture which consists of c. 20% of 2-(3,3-dichlorobutyl)benzenesulfonyl chloride, 35% of 2-(3-chloro-2-buten-1-yl)benzenesulfonyl chloride and 45% of the cis/trans-isomers of 2-(3-chloro-3-buten-1-yl)benzenesulfonyl chloride (analysis by gas chromatography).

EXAMPLE 4

Preparation of 2-(3,3-difluorobutyl)benzenesulfonyl chloride 42.3 g of the mixture of benzenesulfonyl chlorides prepared in Example 3 are reacted in an autoclave at −50° C. with 90 g of hydrogen fluoride. The reaction mixture is then warmed to 18° C. and stirred for 24 hours at 18°-19° C., while expelling hydrogen chloride from the autoclave from time to time. When the reaction is complete, excess hydrogen fluoride is removed with suction and the residue is dissolved in dichloromethane. The solution is washed twice with ice-water, dried over sodium sulfate, and concentrated by evaporation. The residue is filtered through a layer of silica gel with a mixture of 1 part of toluene and 4 parts of hexane and the filtrate is evaporated to dryness, giving 20.4 g of 2-(3,3-difluorobutyl)benzenesulfonyl chloride as an oil. $^1$H-NMR spectroscopy shows that the product contains c. 5% by weight of 2-(3,3-difluorobutyl)benzenesulfonyl fluoride.

EXAMPLE 5

Preparation of 2-(3,3-difluorobutyl)benzenesulfonamide A solution of 26.9 g of 2-(3,3-difluorobutyl)benzenesulfonyl chloride and 200 ml of methylene chloride is added dropwise at 15°-20° C. to a mixture of 50 ml of a 30% solution of ammonia and 50 ml of water, and the reaction mixture is then stirred for 3 hours at 20°-25° C. The methylene chloride phase is separated, washed with water, dried over sodium sulfate and evaporated to dryness. The residue is recrystallised from toluene, giving 19.9 g of 2-(3,3-difluorobutyl)benzenesulfonamide of m.p. 70°-72° C.

EXAMPLE 6

Preparation of 2-(1-bromo-3,3-difluorobutyl)benzenesulfonyl chloride A mixture of 13.4 g of 2-(3,3-difluorobutyl)benzenesulfonyl chloride, 8.6 g of 1,3-dibromo-5,5-dimethylhydantoin and 80 ml of carbon tetrachloride is stirred at 75°-80° C. for 3 hours and simultaneously irradiated with a mercury vapour lamp. The reaction mixture is then evaporated to dryness and the residue is taken up in hexane. The solution is filtered and the filtrate is evaporated to dryness, giving 15.3 g of 2-(1-bromo-3,3-difluorobutyl)benzenesulfonyl chloride as a pale yellow oil. $^1$H-NMR spectroscopy shows that the product contains c. 5% by weight of 2-(1-bromo-3,3-difluorobutyl)benzenesulfonyl fluoride.

EXAMPLE 7

Preparation of 2-(1-bromo-3,3-difluorobutyl)benzenesulfonamide 1.5 g of ammonia are introduced at −5°-0° C. into a solution of 13.9 g of the 2-(1-bromo-3,3-difluorobutyl)benzenesulfonyl chloride in 50 ml of diethyl ether obtained in Example 6 at −5° to 0° C. To the reaction mixture is then added ice-water, followed by 10% hydrochloric acid. The organic phase is separated, washed with water and dried. The solvent is stripped off, giving 11.8 g of 2-(1-bromo-3,3-difluorobutyl)benzenesulfonamide of m.p. 104°-105° C.

EXAMPLE 8

Preparation of 2-(3,3-difluorobuten-1-yl)benzenesulfonamide A solution of 1.52 g of 1,8-diazabicyclo[5.4.0]-undec-7-ene(1.5-5) and 10 ml of dioxane is added dropwise at 20°-25° C. to a solution of 3.3 g of 2-(1-bromo-3,3-difluorobutyl)benzenesulfonamide and 30 ml of dioxane, and the mixture is then stirred for 2 hours. The reaction mixture is poured into water, followed by the steps of acidification with 10% hydrochloric acid, extraction with ethyl acetate, washing the organic extract with water, drying over sodium sulfate, concentration by evaporation and purification of the residue on a column of silica gel. Yield: 0.7 g of 2-(3,3-difluorobuten-1-yl)benzenesulfonamide of m.p. 103°-104° C.

What is claimed is:

1. A process for the preparation of a benzenesulfonamide of general formula

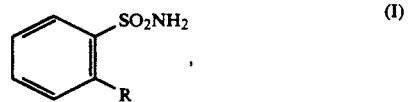

wherein R is 3,3-difluorobutyl (—CH$_2$—CH$_2$—CF$_2$—CH$_3$) or 3,3-difluorobuten-1-yl (—CH=CH—CF$_2$—CH$_3$), which comprises converting a 2-(3-oxobuten-1-yl)benzenesulfonic acid salt of formula II

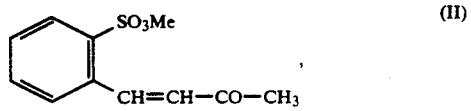

wherein Me is an alkali metal ion or an ammonium ion, by catalytic hydrogenation into a 2-(3-oxobutyl)benzenesulfonic acid salt of formula III

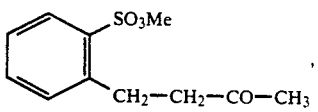 (III)

wherein Me has the above meaning, converting said acid salt of formula (III) by reaction with an inorganic acid chloride into a 2-(3-oxobutyl)benzenesulfonyl chloride of formula IV

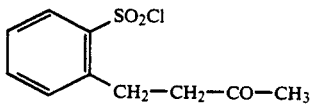 (IV)

then converting said sulfonyl chloride with phosphorus pentachloride into a mixture of benzenesulfonyl chlorides of formula V

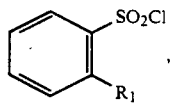 (V)

wherein $R_1$ is 3-chloro-2-buten-1-yl

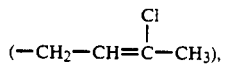, 3-chloro-3-buten-1-yl

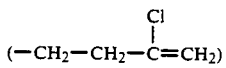

or 3,3-dichlorobutyl ($-CH_2-CH_2-CCl_2-CH_3$), reacting said mixture with hydrogen fluoride to give a mixture of 2-(3,3-difluorobutyl)-benzenesulfohalides of formula VI

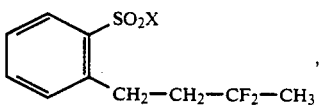 (VI)

wherein X is chloro or fluoro, and converting said mixture either a) by reaction with ammonia into the 2-(3,3-difluorobutyl)benzenesulfonamide of formula Ia

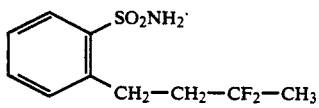 (Ia)

or b) initially with a brominating agent (1,3-dibromo-5,5-dimethylhydantoin) into a mixture of 2-(1-bromo-3,3-difluorobutyl)benzenesulfohalides of formula VII

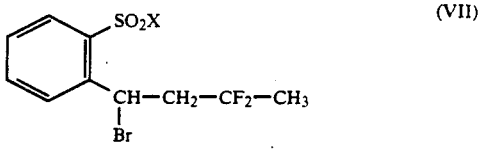 (VII)

wherein X is fluoro or chloro, and then converting this mixture by further reaction with ammonia into the 2-(1-bromo-3,3-difluorobutyl)sulfonamide of formula VIII (VIII)

which is then dehydrobrominated to the 2-(3,3-difluorobuten-1-yl)benzenesulfonamide of formula Ib (Ib)

2. A process according to claim 1, wherein the catalytic hydrogenation of the benzenesulfonic acid salt of formula II is carried out in water as solvent in the temperature range from 0°–50° C. and under a pressure of 1–5 bar in the presence of a palladium or platinum catalyst.

3. A process according to claim 1, wherein the phosgenation of the sulfonic acid salt of formula III is carried out in chlorobenzene as solvent in the temperature range from 70°–90° C. in the presence of a catalytic amount of N,N-dimethylformamide.

4. A process according to claim 1, wherein the reaction of the sulfonyl chloride of formula IV with phosphorus pentachloride is carried out in methylene chloride as solvent in the temperature range from 20°–40° C.

5. A process according to claim 1, wherein the reaction of the mixture of benzenesulfonyl chlorides of formula V with hydrogen fluoride is carried out in the temperature range from 0°–50° C.

6. A process according to claim 1, wherein the reaction of the benzenesulfonyl halides of formula VI or VII is carried out by introducing ammonia into a solution of said sulfonyl halides in an inert solvent in the temperature range from room temperature to 50° C.

7. A process according to claim 1, wherein the bromination of the sulfonyl halide of formula VI is carried out in an aliphatic halogenated hydrocarbon with 1,3-dibromo-5,5-dimethylhydantoin in the presence of a radical former.

* * * * *